United States Patent [19]

Trachewsky

[11] 4,264,601

[45] Apr. 28, 1981

[54] ANTIHYPERTENSIVE AGENTS AND THEIR USE IN TREATMENT OF HYPERTENSION

[75] Inventor: Daniel Trachewsky, Oklahoma City, Okla.

[73] Assignee: The Board of Regents of the University of Oklahoma, Norman, Okla.

[21] Appl. No.: 47,913

[22] Filed: Jun. 12, 1979

[51] Int. Cl.³ ............................................ A61K 31/525
[52] U.S. Cl. .................................................... 424/252
[58] Field of Search .......................................... 424/252

[56] References Cited

U.S. PATENT DOCUMENTS

| 2,388,261 | 11/1945 | Frost | 424/252 |
| 2,650,894 | 9/1953 | Fine | 424/252 |
| 2,847,413 | 8/1958 | Folkers et al. | 424/252 |
| 3,189,598 | 6/1965 | Yagi | 424/252 |
| 3,279,994 | 10/1966 | Koff | 424/252 |
| 3,479,335 | 11/1969 | Blaszczak | 424/252 |
| 3,530,216 | 9/1970 | Cavalli et al. | 424/252 |
| 4,006,216 | 2/1977 | Grybek et al. | 424/252 |

FOREIGN PATENT DOCUMENTS

| 102M | 1/1961 | France | 424/252 |
| 932256 | 7/1963 | United Kingdom | 424/252 |

OTHER PUBLICATIONS

*Chemical Abstracts,* vol. 78, 1973, 69516a.

*Primary Examiner*—Frederick E. Waddell
*Attorney, Agent, or Firm*—Dunlap, Codding & McCarthy

[57] ABSTRACT

Riboflavin analogues, including both endo- and exocyclically substituted isoalloxazines which are competitive inhibitors of the enzyme flavokinase (EC 2.7.1.26) when administered in a non-toxic dosage, effectively reduce the blood pressure of a subject suffering from hypertension.

15 Claims, 4 Drawing Figures

ANTIHYPERTENSIVE AGENTS AND THEIR USE IN TREATMENT OF HYPERTENSION

The invention described herein was made in the course of, or under a grant from, the National Institutes of Health.

BACKGROUND OF THE INVENTION

The present invention relates generally to riboflavin analogues which are competitive inhibitors of the enzyme flavokinase (EC 2.7.1.26). In one aspect the invention relates to a method for reducing blood pressure of a subject suffering from hypertension by administering to such subject an effective, non-toxic dosage of riboflavin analogues which are competitive inhibitors of the enzyme flavokinase. More specifically, but not by way of limitation, the present invention relates to the use of endo- and exocyclically substituted isoalloxazine derivatives as antihypertensive agents for reducing the blood pressure of a subject having hypertension.

It is generally known that expansion of body fluid volumes by renal retention of sodium results in an increase in the blood pressure of an individual. It is further known that certain riboflavin analogues function as competitive inhibitors of the enzyme flavokinase.

I have hertofore reported at the 60th Annual Meeting of the Endocrine Society, held at Miami Beach, Florida during June 14–16, 1978, in a paper entitled "Aldosterone Stimulation of Riboflavin Incorporation into Rat Renal Flavin Coenzymes and the Effect of Inhibition by Riboflavin Analogues on Sodium Reabsorption" and published in the Journal of Clinical Investigation, Volume 62, Number 6, 1325–1333, December 1978, that the administration of aldosterone to adrenalectomized male Sprague-Dawley rats significantly increased the biosynthesis of renal flavin mononucleotide (FMN) and flavin adenine dinucleotide (FAD) in the adrenalectomized male rats. It was further reported that aldosterone significantly decreased the excretion of sodium and increased the excretion of potassium. To determine if the increased biosynthesis of the flavin coenzymes were causing the alterations in urinary sodium and potassium output by aldosterone, the riboflavin analogues, 7,8-dimethyl-10-(2'-hydroxyethyl) isoalloxazine, and 7,8-dimethyl-10-formylmethyl isoalloxazine, were administered to the animals to diminish the conversion of the riboflavin to renal flavin mononucleotide (FMN) by competitively inhibiting the enzyme flavokinase.

The above identified riboflavin analogues, when administered in optimal doses of from about 10 micrograms/100 grams body weight to about 25 micrograms/100 grams body weight effectively opposed the diminished urinary excretion of sodium due to aldosterone. An inverse relationship was detected between the increase in urinary output of sodium and the decrease in renal flavin mononucleotide (FMN) when the animals were treated with aldosterone plus the riboflavin analogue as compared to treatment with the aldosterone alone. The riboflavin analogues reportedly exacted no significant effect on the increased excretion of potassium or on the enhanced synthesis of renal flavin adenine dinucleotide (FAD) by the aldosterone. Further, the analogues alone had no influence on the urinary sodium and potassium output and the renal flavin mononucleotide (FMN) and flavin adenine dinucleotide (FAD) biosynthesis at the dose levels investigated. The conclusion thus reached was that the enhanced synthesis of renal flavin mononucleotide (FMN) may be a causative factor in the increased reabsorption of sodium due to aldosterone and that riboflavin analogues may be employed as a class of antimineralocorticoids.

However, no suggestion was made, nor has it heretofore been considered, that such riboflavin analogues possessed any other biological properties other than as antimineralocorticoids. Further, it is well recognized that excess sodium retention and hypertension are two distinct and separate pathophysicological processes of the human body and one does not necessarily give rise to the other. Thus, the treatment for sodium retention may not be the same as for hypertension and vice versa, and the antimineralocorticoids effective for depleting sodium from the body cannot be predicted as being effective anti-hypertensive agents.

The present invention is the result of original investigative research into the effects of antimineralocorticoids on hypertension, and an object of the present invention is to provide a method for reducing the blood pressure of an individual suffering from hypertension.

Another object of the invention is to provide a compound which, when administered to an individual having hypertension in a non-toxic dosage, effectively reduces the blood pressure of such individual without harmful side effects.

These and other objects, advantages and features of the present invention will be apparent to those skilled in the art from a reading of the following detailed description when read in conjunction with the drawings which accompany the disclosure and with the appended claims.

DETAILED DESCRIPTION

Figure 1:
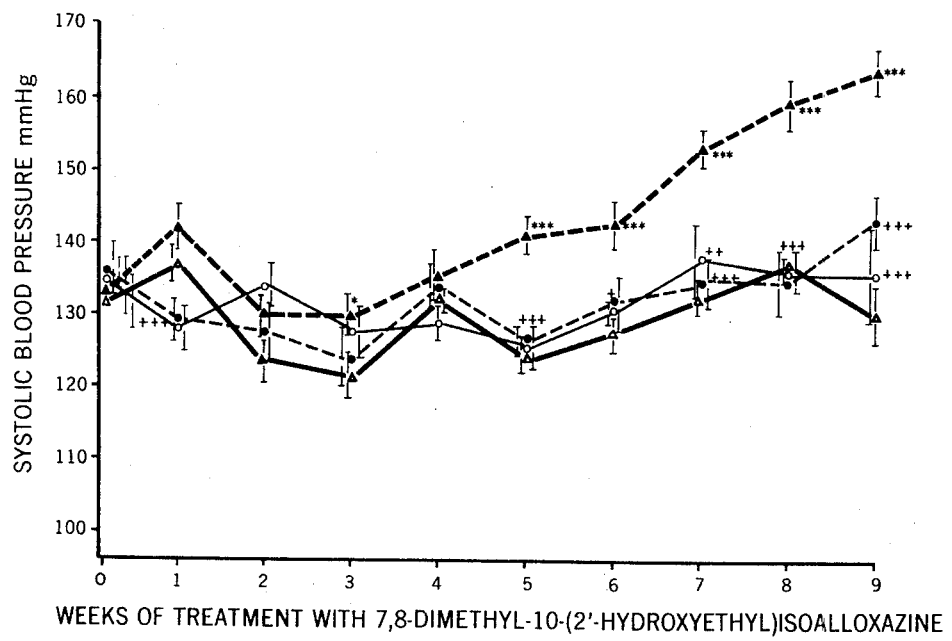
FIG. 1 is a graphic illustration of the effect of 7,8-dimethyl-10-(2'-hydroxyethyl) isoalloxazine as an antihypertensive agent for mineralocorticoid-induced hypertensive rats over a time interval of 9 weeks.

As previously stated, the present invention relates to riboflavin analogues as antihypertensive agents and their uses for reducing blood pressure in hypertension. In order to assist in the understanding of the scope of the invention, as well as the terminology used herein, the following definitions are set forth.

The term "riboflavin analogues" are the endo- and exocyclically substituted isoalloxazines which are competitive inhibitors of the enzyme flavokinase (EC 2.7.1.26) including both the competitive inhibitors which are phosphorylated and non-phosphorylated by flavokinase.

"Competitive inhibitors" are analogues of the substrate (I) which can combine to the active site of the free enzyme (E) in such a manner that it competes with the normal substrate for binding at the active site. A competitive inhibitor reacts reversibly with the enzyme to form an enzyme-inhibitor complex, (EI), analogous to the enzyme substrate complex: E+I=EI. A competitive inhibitor diminishes the rate of catalysis by reducing the proportion of enzyme molecules that have a bound substrate. The hallmark of competitive inhibition is that the inhibition can be overcome at a sufficiently high substrate concentration.

"Phosphorylated riboflavin analogues" are those riboflavin analogues (including, for example, all riboflavin analogues having a 5'-OH group or having a ribityl group attached to the isoalloxazine nucleus at the 10 carbon atom position) which are phosphorylated at the 5'-OH group by flavokinase to analogues of flavin mononucleotide (FMN).

"Non-phosphorylated riboflavin analogues" are riboflavin analogues which are not subject to phosphorylation by the enzyme flavokinase to analogues of flavin mononucleotide (FMN).

"Hypertension" includes both volume mechanisms and vasoconstrictor mechanisms either singularly or in combination. Hypertension or high blood pressure is equal to the product of cardiac output times total peripheral resistance taking into account the many variables that may affect cardiac output and total peripheral resistance.

"Dosage" is the amount of riboflavin analogues administered to a subject during a twenty-four (24) hour period.

The term "subject" as used herein is to be understood to include humans, household animals, such as dogs and cats, and large animals, such as horses or the like.

I have now discovered that hypertension can readily be reduced, and thus controlled, by administering to a subject suffering from hypertension an effective, non-toxic dosage of a riboflavin analogue as defined above. It has now been discovered that riboflavin analogues which are competitive inhibitors of riboflavin for the enzyme flavokinase (EC 2.7.1.26) diminish the conversion of renal riboflavin to renal flavin mononucleotide (FMN) by competitively inhibiting riboflavin at the enzyme flavokinase (EC 2.7.1.26) and thus in turn diminish the conversion of the renal flavin mononucleotide (FMN) to the renal flavin adenine dinucleotide (FAC). Thus, the competitive inhibition of riboflavin for the enzyme flavokinase not only decreases the reabsorption of sodium as a result of aldosterone, but unexpectedly lowers the blood pressure of a subject having hypertension.

Any suitable riboflavin analogue can be employed as an antihypertensive agent to reduce the blood pressure of a subject suffering from hypertension provided that the riboflavin analogue meets the definition heretofore set forth. Illustrative of riboflavin analogues useful as antihypertensive agents for reducing the blood pressure of subjects suffering from hypertension in accordance with the present invention are as follows:

1. Non-phosphorylated Competitive Inhibitors a. 7,8-dimethyl-10-(2'-hydroxyethyl) isoalloxazine
b. 7,8-dimethyl-10-formylmethyl isoalloxazine
c. 5'-deoxyriboflavin
d. riboflavin 5'-(hydrogen sulfate)
e. 10-(2-hydroxyethyl)-7,8-dimethylpyrimido[4,5-b] quinoline-2,-4(3H,-10H)-dione
f. 8-demethyl-8-hydroxyriboflavin
g. All 7,8-dimethyl-10-(ω-hyroxylalkyl) isoallaxazines
  e.g. 1'-DL-glyceryl

1. Non-phosphorylated Competitive Inhibitors -continued

3'-hydroxypropyl
  4'-hydroxybutyl
  5'-hydroxypentyl
  6'-hydroxyhexyl
  } ω-hydroxyalkyl chains h. (3-chlorophenyl)methyl]-7,8-dimethylbenzo[g] pteridine-2,4(3H,10H)-dione
i. 10-[(2,6-dichlorophenyl)methyl]-7,8-dimethylbenzo[g] pteridine-2,4(3H,10H)-dione

2. Phosphorylated Competitive Inhibitors a. 7-chloro-7,8-didemethylriboflavin
b. 1-deoxy-1-(3,4-dihydro-7,8-dimethyl-2,4-dioxopyrido [3,2-g] pteridin-10(2H)-yl)-D-ribitol
c. 7,8-didemethyl-8-chlororiboflavin
d. 6-methylriboflavin
e. 1-deoxy-1-(4-hydroxy-7,8-dimethyl-2-oxopyrido[2,3-b] quinoxalin-10(2H)-yl)-D-ribitol
f. 1-deoxy-1-(2,3-dihydro-7,8-dimethyl-1,3-dioxopyrido [3,4-b]-quinoxalin-5(1H)-yl)-D-ribitol
g. 1-deoxy-1-(3,4-dihydro-7,8-dimethyl-2,4-dioxopyrimido [4,5-b] quinolin-10(2H)-yl)-D-ribitol
h. 1-deoxy-1-(3,4-dihydro-5,7,8-trimethyl-2,4-dioxopyrimido[4,5-b]quinolin-10(2H)-yl)-D-ribitol
i. riboflavin 5-oxide
j. 7,8-dimethylisoalloxazines with the following side chains attached to the 10 position of the parent compound:
  D-erythrityl
  D-allityl
  2'-deoxyribityl While the competitive inhibitor can be phosphorylated or non-phosphorylated, as hereinbefore mentioned, it is peferred that the competitive inhibitor be non-phosphorylated competitive inhibitors since non-phosphorylated competitive inhibitors are more readily removed from the subject because they do not become coenzymes in enzymatic redox reactions within the subject.

The dosage of the riboflavin analogue required to reduce the blood pressure of a subject having hypertension can vary widely and will be dependent, to a large degree, upon the severity and kind of the hypertension, the weight of the subject, the competitive inhibitory property (i.e., $K_i$) of the particular riboflavin analogue employed, and the like. However, it is believed that the dosage would not exceed a level of about 14 milligrams, and will generally range from about 100 micrograms to about 14 milligrams. In the case of a subject suffering from vasoconstrictor hypertension, the dosage of the riboflavin analogues will generally range from about 100 micrograms to about 2 milligrams.

The method of administration of the riboflavin analogue can be by any suitable means, such as injection, oral administration, and the like. As is evident, when the riboflavin analogue is administered by injection, the riboflavin analogue will be dissolved in a suitable vehicle for the analogue, such as a dilute aqueous solution of sodium chloride.

As previously indicated, it is believed that any suitable riboflavin analogue can be employed as an antihypertensive agent in reducing hypertension in an individual provided that the riboflavin analogue falls within the definition of same heretofore set forth.

Mineralocorticoid hypertension induced by chronic administration of deoxycorticosterone acetate(4-pregnen-21-ol-3,20-dione acetate) to rats in conjunction with saline loading, simulates in some respects, the syndrome of hypertension in humans. Accordingly, rats with mineralocorticoid hypertension have heretofore been used for evaluating antihypertensive agents and the like.

The following examples are given to illustrate the effectiveness of riboflavin analogues in reducing blood pressure. The examples are for illustrative purposes only and are not to be construed as unduly limiting the scope of the invention as hereinafter recited in the claims. All parts and percentages in the examples, unless otherwise specified, are parts by weight and weight percentages, and blood pressure values are mm of mercury.

EXAMPLE 1

Fifty-five male Sprague-Dawley rats weighing from 97 grams to 183 grams underwent right adrenonephrectomy under pentobarbital anesthesia (5 mg/100 g body wt). Following surgery all rats were given 0.2 milliliter of penicillin for five to six days and were placed on one percent (1%) sodium chloride drinking water and Purina Rat Chow, a normal rat feed manufactured and marketed by the Ralston Purina Company, Inc., of St. Louis, Missouri. The Rat Chow contained 0.062 milliequivalents of sodium per gram of feed and 0.282 milliequivalents of potassium per gram of feed. Three days following surgery the animals were divided into a plurality of weight-matched groups, and the systolic blood pressure and heart rates of the unanesthetized animals were measured for four weeks prior to the initiation of treatment using the tail cuff plethysmographic method in order to condition the rats to this method of recording the systolic blood pressure and heart rates. The tail cuff employed to obtain the indirect systolic blood pressure was a 15 millimeter by 15 millimeter (diameter by length) occlusion cuff which was placed at the back of the tail of each of the rats. The occlusion cuff was connected to an inflation bulb and, by a T-tube connection, to a Statham P23 ID transducer. Continuous recordings of cuff pressure were performed using a two channel Hewlett Packard 7702B recorder. A pulse transducer manufactured and marketed by Buffington Clinical Devices, Cleveland, Ohio, was applied with tape to the ventral surface of the tail immediately distal to the occluding cuff.

During the investigation, the animals were housed in plastic cages, two rats per cage in most instances, and occasionally three rats per cage. The animals were maintained in a room with a constant temperature of 23° C. and automatic light control with dark periods of from 6:00 p.m. until 6:00 a.m. the following day. The initial division of the animals was into six groups, Group I (the control group) containing 10 animals and the remaining five groups containing 9 animals each. The particular division of the animals into the various groups was by random selection and to provide substantially weightmatched groups. Since all of the animals, except those in Group I, the control group, were to be, and in fact were, injected with deoxycorticosterone acetate to create hypertensive rats, the animals separated into Groups II, V and VI were combined and are hereinafter designated collectively as Group II.

The weekly mean systolic blood pressure of the rats of Groups, I, II, III and IV during the conditioning phase of the investigation are tabulated in Table I.

TABLE I

| Conditioning of the Animals | | | | |
| --- | --- | --- | --- | --- |
| | Group I | Group II | Group III | Group IV |
| Week No. 1 | | | | |
| No. of animals tested | 9 | 7 | 3 | 3 |
| No. of Measurements | 54 | 42 | 18 | 18 |
| Mean Value Blood Pressure | 131.78 | 149.71 | 157.00 | 147.00 |
| Standard Deviation | 12.35 | 9.41 | 18.36 | 11.79 |
| Standard Error | 4.12 | 3.56 | 10.60 | 6.81 |
| Week No. 2 | | | | |
| No. of animals tested | 20 | 35 | 14 | 11 |
| No. of Measurements | 120 | 210 | 84 | 66 |
| Mean Value Blood Pressure | 145.25 | 139.51 | 143.43 | 147.55 |
| Standard Deviation | 12.06 | 23.12 | 9.28 | 12.29 |
| Standard Error | 2.70 | 3.91 | 2.48 | 3.71 |
| Week No. 3 | | | | |
| No. of animals tested | 15 | 19 | 10 | 10 |
| No. of Measurements | 90 | 114 | 60 | 60 |
| Mean Value Blood Pressure | 136.20 | 135.00 | 146.90 | 138.30 |
| Standard Deviation | 12.31 | 16.49 | 12.09 | 14.94 |
| Standard Error | 3.18 | 3.78 | 3.82 | 4.72 |
| Week No. 4 | | | | |
| No. of animals tested | 14 | 17 | 12 | 10 |
| No. of Measurements | 84 | 102 | 72 | 60 |
| Mean Value Blood Pressure | 131.79 | 133.00 | 138.33 | 137.00 |
| Standard Deviation | 13.18 | 11.96 | 11.64 | 5.46 |
| Standard Error | 3.52 | 2.90 | 3.36 | 1.73 |

Hypertension was induced in the conditioned rats by administering 3.0 milligrams of deoxycorticosterone acetate, manufactured by Steraloids, Inc., Wilton, N.H., suspended in 1.0 milliliter of sesame oil. The deoxycorticosterone acetate was administered to each rat in Groups II, III, and IV twice weekly by subcutaneous injection for a period of nine weeks. Two groups of rats, namely Groups III and IV, received in addition to the deoxycorticosterone acetate, simultaneous doses of 1.2 milligrams (in 1.5 milliliters of 0.45% sodium chloride) or 1.6 milligrams (in 2.0 milliliters of 0.45% sodium chloride), respectively, of the riboflavin analogue 7,8-dimethyl-10-(2'-hydroxyethyl) isoalloxazine. Group I, the control group of rats, received only the sesame oil and the 0.45% sodium chloride for injection. Systolic blood pressure and heart rates were measured in the rats of each group on the day following injection of either of the vehicles, the deoxycorticosterone acetate or the mixture of the deoxycorticosterone acetate and the riboflavin analogue. Six measurements were made on each animal tested at each weekly interval in order to determine the mean blood pressure for each animal. Blood pressure values above 150 mm mercury were regarded as hypertensive. Tabulated in Table II are the weekly mean systolic blood pressure measurements made on the animals during the 9 week treatment period.

TABLE II

| Treatment of the Animals | | | | |
|---|---|---|---|---|
| | Group I (CONTROL) | Group II[a] | Group III[b] | Group IV[c] |
| Week No. 1 | | | | |
| No. of animals tested | 11 | 11 | 8 | 8 |
| No. of Measurements | 66 | 66 | 48 | 48 |
| Mean Value Blood Pressure | 137 | 142 | 129 | 128 |
| Standard Deviation | 8.17 | 9.43 | 8.63 | 9.10 |
| Standard Error | 2.46 | 2.84 | 3.05 | 3.22 |
| Week No. 2 | | | | |
| No. of animals tested | 11 | 13 | 10 | 9 |
| No. of Measurements | 66 | 78 | 60 | 54 |
| Mean Value Blood Pressure | 123.45 | 129.85 | 127.70 | 134.22 |
| Standard Deviation | 9.67 | 11.72 | 13.53 | 9.05 |
| Standard Error | 2.92 | 3.25 | 4.28 | 3.02 |
| Week No. 3 | | | | |
| No. of animals tested | 7 | 12 | 6 | 7 |
| No. of Measurements | 42 | 72 | 36 | 42 |
| Mean Value Blood Pressure | 121.43 | 129.58 | 123.67 | 127.71 |
| Standard Deviation | 8.16 | 10.08 | 12.83 | 9.84 |
| Standard Error | 3.08 | 2.91 | 5.24 | 3.72 |
| Week No. 4 | | | | |
| No. of animals tested | 14 | 17 | 9 | 8 |
| No. of Measurements | 84 | 102 | 54 | 48 |
| Mean Value Blood Pressure | 132.14 | 135.41 | 133.33 | 128.75 |
| Standard Deviation | 6.44 | 14.09 | 8.94 | 7.92 |
| Standard Error | 1.72 | 3.42 | 2.98 | 2.80 |
| Week No. 5 | | | | |
| No. of animals tested | 13 | 19 | 10 | 7 |
| No. of Measurements | 78 | 114 | 60 | 42 |
| Mean Value Blood Pressure | 124.38 | 141.05 | 125.50 | 125.00 |
| Standard Deviation | 8.25 | 11.94 | 6.90 | 7.64 |
| Standard Error | 2.29 | 2.74 | 2.18 | 2.89 |
| Week No. 6 | | | | |
| No. of animals tested | 11 | 13 | 7 | 5 |
| No. of Measurements | 66 | 78 | 42 | 30 |
| Mean Value Blood Pressure | 127.55 | 142.31 | 131.29 | 130.75 |
| Standard Deviation | 7.90 | 11.74 | 11.42 | 2.49 |
| Standard Error | 2.38 | 3.26 | 4.32 | 1.24 |
| Week No. 7 | | | | |
| No. of animals tested | 14 | 18 | 9 | 9 |
| No. of Measurements | 84 | 108 | 54 | 54 |
| Mean Value Blood Pressure | 132.43 | 152.83 | 134.55 | 137.77 |
| Standard Deviation | 9.85 | 11.21 | 10.36 | 14.85 |
| Standard Error | 2.63 | 2.64 | 3.45 | 4.95 |
| Week No. 8 | | | | |
| No. of animals tested | 12 | 18 | 10 | 9 |
| No. of Measurements | 72 | 108 | 60 | 54 |
| Mean Value Blood Pressure | 136.75 | 158.83 | 134.50 | 136.00 |
| Standard Deviation | 7.86 | 15.71 | 14.63 | 8.72 |
| Standard Error | 2.27 | 3.70 | 4.63 | 2.91 |
| Week No. 9 | | | | |
| No. of animals tested | 12 | 19 | 9 | 7 |
| No. of Measurements | 72 | 114 | 54 | 42 |
| Mean Value Blood Pressure | 130.08 | 163.16 | 135.56 | 143.29 |
| Standard Deviation | 13.01 | 13.41 | 19.44 | 9.01 |
| Standard Error | 3.76 | 3.08 | 6.48 | 3.41 |

[a] Treated with deoxycorticosterone acetate
[b] deoxycorticosterone acetate + 1.2 mg. 7,8-dimethyl-10-(2'-hydroxyethyl) isoalloxazine
[c] deoxycorticosterone acetate + 1.6 mg. 7,8-dimethyl-10-(2'-hydroxyethyl) isoalloxazine The weekly mean systolic blood pressure measurements provide the data points of the graph of FIG. 1. The weekly mean systolic blood pressure measurements of the 4th week of the conditioning period represents the 0 week on the graph of FIG. 1. The points on the graphs representing the mean blood pressure values of the four groups of animals are designated as follows:

Δ - Group I (Control)
▲ - Group II
● - Group III
O - Group IV

In order to eliminate, as much as possible, variations in the readings of the systolic blood pressure of the animals during the experiments, the animals were warmed with an infra-red lamp (ambient temperature of 35° C. to 40° C.) until the arterial pulse displacements were nearly full scale. The indirect systolic pressure measurements were then obtained by increasing the pressure of the occlusion cuff until the arterial pulse displacements were no longer apparent and then gradually releasing cuff pressure. The cuff pressure at which the first real pulse displacement appeared was defined as the systolic pressure. The systolic pressures were recorded by the same person and at approximately the same time of the day through the entire investigation.

The data above, as depicted in FIG. 1, clearly illustrates that the systolic blood pressures of the rats rose significantly after four weeks of biweekly treatment with 3.0 milligrams of deoxycorticosterone acetate. The blood pressure of the rats remained in the hypertensive range until the end of the ninth week at which time the animals were sacrificed. The systolic blood pressures of the rats administered deoxycorticosterone acetate averaged above 163±3 millimeters mercury (standard error of the mean) compared to the controls of about 133±3 millimeters mercury. The elevation in the systolic blood pressures of the rats noted after the fourth week when deoxycorticosterone acetate was administered was not evident when either the 1.2 milligrams or the 1.6 milligrams of 7,8-dimethyl-10-(2'-hydroxyethyl) isoalloxazine were administered simultaneously to the rats. It should be noted that there was no significant differences in the blood pressure among the four groups of rats at the end of the fourth week of the conditioning period and prior to the initiation of therapy (e.g., 0 week on FIG. 1).

Figure 3:
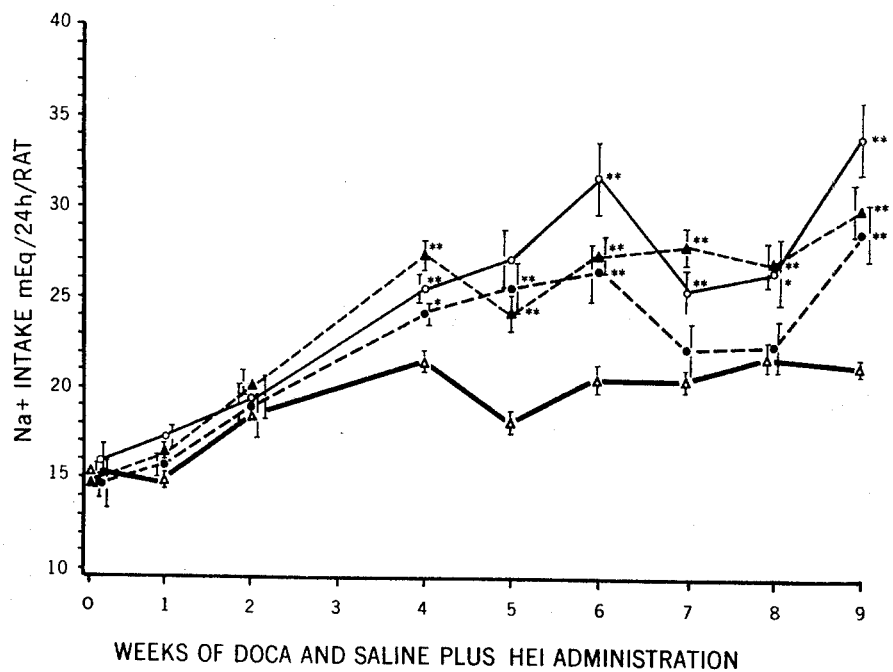
FIG. 3 is a graphic illustration depicting the sodium intake in milliequivalents per 24 hour period per rat of various groups of rats including control and treated rats, over a period of 9 weeks.

In addition to the measurement of the systolic blood pressure of the animals, weekly sodium intake studies were simultaneously carried out on the conditioned rats. The intake of the drinking water, an aqueous 1% sodium chloride solution, was measured during four separate 24 hour periods each week, and the daily food intake of known sodium content was also measured. A mean weekly sodium intake was thus calculated on the basis of the four daily food and 24 hour drinking water consumptions of the animals. The mean weekly sodium intake determinations are tabulated in Table III. Such determinations provide the data points in the graph of FIG. 3.

TABLE III

| | Treatment of the Animals | | | |
|---|---|---|---|---|
| | Group I (CONTROL) | Group II[a] | Group III[b] | Group IV[c] |
| Week No. 1 | | | | |
| No. of separate measurements of combined daily food and drinking water consumptions | 60 | 70 | 30 | 30 |
| Mean Value Sodium Intake mEq/24 hours/Rat | 13.80 | 16.35 | 15.86 | 17.15 |
| Standard Deviation | 2.59 | 2.86 | 3.27 | 2.99 |
| Standard Error | 0.33 | 0.34 | 0.60 | 0.55 |
| Week No. 2 | | | | |
| No. of separate measurements of combined daily food and drinking water consumptions | 15 | 20 | 10 | 10 |
| Mean Value Sodium Intake mEq/24 hours/Rat | 18.35 | 20.21 | 18.84 | 19.36 |
| Standard Deviation | 4.71 | 3.07 | 3.95 | 3.87 |
| Standard Error | 1.22 | 0.69 | 1.25 | 1.23 |
| Week No. 3 - No measurements were taken. | | | | |
| Week No. 4 | | | | |
| No. of separate Measurements of combined daily food and drinking water consumptions | 43 | 60 | 30 | 27 |
| Mean Value Sodium Intake mEq/24 hours/Rat | 21.33 | 27.18 | 23.96 | 25.34 |
| Standard Deviation | 4.63 | 5.98 | 3.31 | 4.43 |
| Standard Error | 0.71 | 0.77 | 0.60 | 0.85 |
| Week No. 5 | | | | |
| No. of separate Measurements of combined daily food and drinking water consumptions | 30 | 48 | 30 | 26 |
| Mean Value Sodium Intake mEq/24 hours/Rat | 17.95 | 23.91 | 25.39 | 27.06 |
| Standard Deviation | 3.04 | 7.24 | 7.91 | 8.41 |
| Standard Error | 0.55 | 1.04 | 1.45 | 1.65 |
| Week No. 6 | | | | |
| No. of separate measurements of combined daily food and drinking water consumptions | 45 | 46 | 20 | 18 |
| Mean Value Sodium Intake mEq/24 hours/Rat | 20.40 | 27.21 | 26.40 | 31.34 |
| Standard Deviation | 5.20 | 6.48 | 7.62 | 8.45 |
| Standard Error | 0.78 | 0.96 | 1.70 | 1.99 |
| Week No. 7 | | | | |
| No. of separate Measurements of combined daily food and drinking water consumptions | 30 | 46 | 30 | 27 |
| Mean Value Sodium Intake mEq/24 hours/Rat | 20.17 | 27.55 | 22.08 | 25.25 |
| Standard Deviation | 3.12 | 6.31 | 8.25 | 6.72 |
| Standard Error | 0.57 | 0.93 | 1.51 | 1.29 |
| Week No. 8 | | | | |
| No. of separate measurements of combined daily food and drinking water consumptions | 30 | 46 | 30 | 27 |
| Mean Value Sodium Intake mEq/24 hours/Rat | 21.39 | 26.70 | 22.06 | 26.69 |
| Standard Deviation | 4.37 | 8.03 | 7.33 | 9.08 |
| Standard Error | 0.80 | 1.18 | 1.34 | 1.75 |
| Week No. 9 | | | | |
| No. of separate measurements of combined daily food and drinking water consumptions | 45 | 58 | 30 | 27 |
| Mean Value Sodium Intake mEq/24 hours/Rat | 20.97 | 29.52 | 28.43 | 33.56 |
| Standard Deviation | 2.87 | 10.69 | 8.38 | 10.81 |
| Standard Error | 0.43 | 1.40 | 1.53 | 2.08 |

[a] Treated with deoxycorticosterone acetate
[b] deoxycorticosterone acetate + 1.2 mg. 7,8-dimethyl-10-(2'-hydroxyethyl) isoalloxazine
[c] deoxycorticosterone acetate + 1.6 mg. 7,8-dimethyl-10-(2'-hydroxyethyl) isoalloxazine The points representing the mean weekly sodium intake values of the four groups of animals are designated as follows:

Δ - Group I (Control)
▲ - Group II
⊙ - Group III
○ - Group IV

Blood samples of about 5 milliliters were taken at the end of the 9 week period of investigation via decapitation of the animals and collection of the blood in tubes through a funnel wetted with 25 mM of the free acid EGTA, ethyleneglycol-bis(B-aminoethyl ether)-N,N'-tetraacetic acid, manufactured and marketed by the Sigma Chemical Co., St. Louis, Missouri. The EGTA was used to prevent immediate clotting in the funnel stem. Following collection, the blood was allowed to clot and the sera was collected.

Following decapitation, a specimen of approximately 1.5 grams of the left iliopsoas muscle of each rat was excised, weighed and frozen for subsequent tissue electrolyte determination. All sera sodium and potassium determinations were made using an Instrumentation Laboratory Model IL 443 flame photometer (Instrumentation Laboratory, Inc., Lexington, Mass.). For measurement of the sodium and potassium concentration in the muscle tissue, the specimens of control and treated animals were thawed and processed simultaneously. The wet weight of each sample was taken and the sample dried at 110° C. for 48 hours in glass crucibles. No additional weight loss was found by drying longer than the 48 hour period. After recording the dry weight, the samples were ashed at 550° C. for 24 hours using a Thermodyne-type 1400 furnace and then the samples were cooled. Following the ashing procedure, the white ashes were digested in 0.5 milliliters of concentrated nitric acid and the contents of the crucibles were evaporated on a hot plate. The contents of the crucibles were again ashed at 550° C. for 24 hours and then cooled; 0.1 milliliter of concentrated nitric acid was then added to each crucible and, thereafter, 1.0 milliliter of 0.5 N nitric acid was added. The contents of each crucible were transferred to separate 10.0 milliliter volumetric flasks; each crucible was rinsed twice more with 1.0 milliliter of the 0.5 N nitric acid, thus providing a total liquid volume of 3.1 milliliter; and each crucible was rinsed three times with deionized water, thereby bringing the total volume of the contents in each volumetric flask to 10.0 milliliters. The sodium and potassium contents of each flask were determined by a flame photometer, and the sodium and potassium concentrations in the iliopsoas tissue were expressed in microequivalents per gram dry weight. The water contents of the specimen were calculated by the formula (weight loss after drying per wet weight)×100.

Table IV is a tabulation of the sodium concentration and the potassium concentration detected in the iliopsoas muscle of the sacrificed animals of Groups I–IV.

TABLE IV

EFFECT OF NINE WEEKS OF ADMINISTRATION OF 7,8-DIMETHYL-10-(2'-HYDROXYETHYL) ISOALLOXAZINE ON THE SODIUM AND POTASSIUM CONTENTS OF THE ILIOPSOAS MUSCLE OF DEOXYCORTICOSTERONE ACETATE-SALT HYPERTENSIVE RATS

| Treatment Group No. | Number of Rats | Sodium µeq/q Dry Wt | Potassium µeq/q Dry Wt |
|---|---|---|---|
| I (CONTROL) | 15 | 184 ± 7 | 311 ± 10 |
| II[a] | 20 | 223 ± 5 | 273 ± 7 |
| III[b] | 10 | 216 ± 8 | 268 ± 10 |
| IV[c] | 9 | 196 ± 11 | 274 ± 15 |

[a]Treated with deoxycorticosterone acetate
[b]deoxycorticosterone acetate + 1.2 mg. 7,8-dimethyl-10-(2'-hydroxyethyl) isoalloxazine
[c]deoxycorticosterone acetate + 1.6 mg. 7,8-dimethyl-10-(2'-hydroxyethyl) isoalloxazine The tabulated data of Table IV illustrates that the administration of 1.6 milligrams of 7,8-dimethyl-10-(2'-hydroxyethyl) isoalloxazine reduced the sodium concentration in the iliopsoas muscle of the animals tested.

The administration of the deoxycorticosterone acetate to the animals increased the water content of the iliopsoas muscle of the animals by an average value of 0.7 percent; whereas the treatment of the animals with deoxycorticosterone acetate in combination with 1.6 milligrams of 7,8-dimethyl-10-(2'-hydroxyethyl) isoalloxazine, reduced the water content of the iliopsoas muscle of the animals to approximately the same level as the control animals. Table V summarizes the effect of deoxycorticosterone acetate and the combination of deoxycorticosterone acetate and 7,8-dimethyl-10-(2'-hydroxyethyl) isoalloxazine on the water content of the iliopsoas muscle of the test animals.

TABLE V

INFLUENCE OF NINE WEEKS OF ADMINISTRATION OF 7,8-DIMETHYL-10-(2'-HYDROXYETHYL) ISOALLOXAZINE ADMINISTRATION ON THE WATER CONTENT OF THE ILIOPSOAS MUSCLE OF DEOXYCORTICOSTERONE ACETATE-SALT HYPERTENSIVE RATS

| Treatment Group No. | Number of rats | Water Content % |
|---|---|---|
| I (CONTROL) | 15 | 75.82 ± 0.26 |
| II[a] | 20 | 76.31 ± 0.09 |
| III[b] | 10 | 76.07 ± 0.24 |
| IV[c] | 9 | 75.64 ± 0.28 |

[a]Treated with deoxycorticosterone acetate
[b]deoxycorticosterone acetate + 1.2 mg. 7,8-dimethyl-10-(2'-hydroxyethyl) isoalloxazine
[c]deoxycorticosterone acetate + 1.6 mg. 7,8-dimethyl-10-(2'-hydroxyethyl) isoalloxazine The data set forth in Tables IV and V illustrates that deoxycorticosterone acetate resulted in an average 21 percent increase in the sodium content of the iliopsoas muscle of the animals and an average 0.7 percent increase in the water content of the muscle. Such data suggests that deoxycorticosterone acetate causes a positive sodium balance in the animal. However, the data further suggests that 7,8-dimethyl-10-(2'-hydroxyethyl) isoalloxazine effectively reduces the positive sodium balance caused by the deoxycorticosterone acetate.

In addition, Table VI summarizes the effect of deoxycorticosterone acetate and varying amounts of the riboflavin analogue 7,8-dimethyl-10-(2'-hydroxyethyl) isoalloxazine on the heart and kidney weights of the treated animals.

TABLE VI

SUMMATION OF THE EFFECT OF NINE WEEKS OF RIBOFLAVIN ANALOGUE 7,8-DIMETHYL-10-(2'HYDROXYETHYL) ISOALLOXAZINE ADMINISTRATION ON THE ORGAN WEIGHTS OF DEOXYCORTICOSTERONE ACETATE-SALT HYPERTENSIVE RATS

| Treatment Group No. | Number of Rats | Average Heart wt (g) | Average Heart wt 100g Body wt (g) | Average Kidney wt (g) | Average Kidney wt 100g Body wt (g) |
|---|---|---|---|---|---|
| I (CONTROL) | 15 | 1.36 ± 0.03 | 0.29 ± 0.01 | 2.57 ± 0.07 | 0.56 ± 0.01 |
| II[a] | 20 | 1.51 ± 0.04 | 0.32 ± 0.01 | 2.97 ± 0.11 | 0.62 ± 0.02 |

TABLE VI-continued
SUMMATION OF
THE EFFECT OF NINE WEEKS OF RIBOFLAVIN ANALOGUE
7,8-DIMETHYL-10-(2'HYDROXYETHYL) ISOALLOXAZINE
ADMINISTRATION ON THE ORGAN WEIGHTS OF
DEOXYCORTICOSTERONE ACETATE-SALT HYPERTENSIVE RATS

| Treatment Group No. | Number of Rats | Average Heart wt (g) | Average Heart wt 100g Body wt (g) | Average Kidney wt (g) | Average Kidney wt 100g Body wt (g) |
|---|---|---|---|---|---|
| III[b] | 10 | 1.56 ± 0.04 | 0.33 ± 0.01 | 3.11 ± 0.11 | 0.65 ± 0.03 |
| IV[c] | 9 | 1.60 ± 0.05 | 0.34 ± 0.01 | 3.16 ± 0.11 | 0.67 ± 0.03 |

[a]Treated with deoxycorticosterone acetate
[b]deoxycorticosterone acetate + 1.2 mg. 7,8-dimethyl-10-(2'-hydroxyethyl) isoalloxazine
[c]deoxycorticosterone acetate + 1.6 mg. 7,8-dimethyl-10-(2'-hydroxyethyl) isoalloxazine The above data clearly shows that deoxycorticosterone acetate either singularly or in combination with the riboflavin analogue had an effect upon the heart and kidney weights of the animals treated with same.

EXAMPLE 2

Fifty-eight male Sprague-Dawley rats weighing from 137 grams to 237 grams underwent right adrenonephrectomy under pentobarbital anesthesia (5 mg/100 mg body wt). Following surgery all rats were given 0.1 milliliter of penicillin for six days and were placed on one percent (1%) sodium chloride drinking water and Purina Rat Chow, a normal rat feed manufactured and marketed by the Ralston Purina Company, Inc., of St. Louis, Missouri. The Rat Chow contained 0.062 milliequivalents of sodium per gram of feed and 0.282 milliequivalents of potassium per gram of feed. Three days following surgery the systolic blood pressure and heart rates of the unanesthetized animals were measured using the tail cuff plethysmographic method for two weeks prior to the initiation of treatment in order to condition the rats to this method of recording the systolic blood pressure and heart rates. The tail cuff employed to obtain the indirect systolic blood pressure was a 15 millimeter by 15 millimeter (diameter by length) occlusion cuff which was placed at the back of the tail of each of the rats. The occlusion cuff was connected to an inflation bulb and, by a T-tube connection, to a Statham P23 ID transducer. Continuous recordings of cuff pressure were performed using a two-channel Hewlett Packard 7702B recorder. A pulse transducer, manufactured and marketed by Buffington Clinical Devices, Cleveland, Ohio, was applied with tape to the ventral surface of the tail immediately distal to the occluding cuff.

During the investigation, the animals were housed in plastic cages, two rats per cage in most instances, and occasionally three rats per cage. The animals were maintained in a room with a constant temperature of 23° C. and automatic light control with dark periods of from 6:00 p.m. until 6:00 a.m. the following day. After the initial adaption of the animals to the environment, the animals were divided into a plurality of weight-matched groups. The initial division of the animals was into five groups, Group I (the control group) containing 15 animals, Group II containing 16 animals, Group III containing 8 animals, Group IV containing 8 animals, and Group V containing 8 animals. Three of the animals did not survive surgery. Since all the animals, except those in Group I, the control group, were to be, and in fact were, injected with deoxycorticosterone acetate to create hypertensive rats, the animals separated into Groups II and V were combined and are hereinafter designated collectively as Group II.

The weekly mean systolic blood pressure of the rats of Groups I, II, III and IV during the conditioning phase of the investigation are tabulated in Table VII.

TABLE VII

| | Conditioning of the Animals | | | |
|---|---|---|---|---|
| | Group I | Group II | Group III | Group IV |
| Week No. 1 | | | | |
| No. of animals tested | 26 | 27 | 9 | 9 |
| No. of Measurements | 156 | 162 | 54 | 54 |
| Mean Value Blood Pressure | 149.31 | 150.78 | 147.33 | 157.56 |
| Standard Deviation | 13.86 | 16.02 | 14.29 | 9.68 |
| Standard Error | 2.72 | 3.08 | 4.76 | 3.23 |
| Week No. 2 | | | | |
| No. of animals tested | 25 | 46 | 17 | 11 |
| No. of Measurements | 150 | 276 | 102 | 66 |
| Mean Value Blood Pressure | 144.92 | 145.00 | 151.35 | 145.91 |
| Standard Deviation | 10.67 | 14.82 | 8.25 | 16.61 |
| Standard Error | 2.13 | 2.19 | 2.00 | 5.01 |

Hypertension was induced in the conditioned rats by administering 3.0 milligrams of deoxycorticosterone acetate, manufactured by Steraloids, Inc., Wilton, N.H., suspended in 1.0 milliliter of sesame oil. The deoxycorticosterone acetate was administered to each rat in Groups II, III, and IV twice weekly by subcutaneous injection for a period of nine weeks. Two other groups of rats, namely Groups III and IV, received in addition to the deoxycorticosterone acetate, simultaneous doses of 1.2 milligrams (in 1.5 milliliters of 0.45% sodium chloride) or 1.6 milligrams (in 2.0 milliliters of 0.45% sodium chloride), respectively, of the riboflavin analogue 7,8-dimethyl-10-formylmethyl isoalloxazine. Group I, the control group of rats, received only the sesame oil and the 0.45% sodium chloride for injection. Systolic blood pressure and heart rates were measured in the rats of each group on the day following injection of either of the vehicles, the deoxycorticosterone acetate or the mixture of the deoxycorticosterone acetate and the riboflavin analogue. Six measurements were made on each animal tested at each weekly interval in order to determine the mean blood pressure for each animal. Blood pressure values above 150 mm mercury were regarded as hypertensive. Tabulated in Table VIII are the weekly mean systolic blood pressure measurements made on the animals during the 8 week test period.

TABLE VIII

| | Treatment of the Animals | | | |
|---|---|---|---|---|
| | Group I (CONTROL) | Group II[a] | Group III[b] | Group IV[c] |
| Week No. 1 | | | | |
| No. of animals tested | 26 | 27 | 9 | 8 |
| No. of Measurements | 156 | 162 | 54 | 48 |
| Mean Value Blood Pressure | 148.50 | 143.89 | 142.33 | 146.00 |
| Standard Deviation | 10.04 | 16.01 | 13.24 | 17.74 |
| Standard Error | 2.01 | 3.08 | 4.41 | 6.27 |
| Week No. 2 | | | | |
| No. of animals tested | 30 | 30 | 10 | 16 |
| No. of Measurements | 180 | 180 | 60 | 96 |
| Mean Value Blood Pressure | 148.23 | 151.93 | 149.00 | 149.81 |
| Standard Deviation | 13.38 | 16.30 | 16.08 | 14.71 |
| Standard Error | 2.44 | 2.98 | 5.08 | 3.68 |
| Week No. 3 | | | | |
| No. of animals tested | 17 | 24 | 13 | 7 |
| No. of Measurements | 102 | 144 | 78 | 42 |
| Mean Value Blood Pressure | 150.00 | 151.58 | 157.54 | 137.43 |
| Standard Deviation | 16.76 | 17.73 | 15.52 | 23.96 |
| Standard Error | 4.06 | 3.62 | 4.30 | 9.06 |
| Week No. 4 | | | | |
| No. of animals tested | 10 | 14 | 10 | 5 |
| No. of Measurements | 60 | 84 | 60 | 30 |
| Mean Value Blood Pressure | 137.80 | 147.93 | 148.30 | 131.60 |
| Standard Deviation | 12.96 | 14.67 | 12.42 | 17.04 |
| Standard Error | 4.10 | 3.92 | 3.93 | 7.62 |
| Week No. 5(A) | | | | |
| No. of animals tested | 18 | 22 | 9 | 10 |
| No. of Measurements | 108 | 132 | 54 | 60 |
| Mean Value Blood Pressure | 136.06 | 163.00 | 161.22 | 140.40 |
| Standard Deviation | 14.21 | 18.30 | 12.50 | 14.46 |
| Standard Error | 3.35 | 3.90 | 4.17 | 4.57 |
| Week No. 6(A) | | | | |
| No. of animals tested | 13 | 16 | 9 | 10 |
| No. of Measurements | 78 | 96 | 54 | 60 |
| Mean Value Blood Pressure | 134.77 | 164.94 | 139.00 | 139.60 |
| Standard Deviation | 10.15 | 18.26 | 23.06 | 14.53 |
| Standard Error | 2.81 | 4.57 | 7.69 | 4.60 |
| Week No. 7(A) | | | | |
| No. of animals tested | 14 | 24 | 16 | 6 |
| No. of Measurements Mean Value | 84 | 144 | 96 | 36 |
| Blood Pressure | 124.29 | 162.65 | 143.88 | 135.33 |
| Standard Deviation | 16.59 | 29.29 | 17.26 | 14.35 |
| Standard Error | 4.43 | 5.98 | 4.31 | 5.86 |
| Week No. 8(A) | | | | |
| No. of animals tested | 13 | 18 | 15 | 9 |
| No. of Measurements | 78 | 108 | 90 | 54 |
| Mean Value Blood Pressure | 119.92 | 159.17 | 144.67 | 130.44 |
| Standard Deviation | 15.05 | 15.93 | 16.11 | 17.97 |
| Standard Error | 4.17 | 3.75 | 4.16 | 6.00 |

(A) Data collected after week of disturbances as set forth below.
[a] Treated with deoxycorticosterone acetate
[b] deoxycorticosterone acetate + 1.2 mg. 7,8-dimethyl-10-formylmethyl isoalloxazine
[c] deoxycorticosterone acetate + 1.6 mg. 7,8-dimethyl-10-formylmethyl isoalloxazine During the fifth week of the eight week study, the animals were disturbed. This was evident because of their behavior and the fact that the animals would not cooperate in the testing program. Thus, data gathered during the fifth week was invalid as considered in keeping with standard and acceptable research procedure. To compensate for the unacceptable data, the eight week test was in fact conducted for a total period of nine weeks but the data from only eight weeks of testing was evaluated. Data collected during the initial fifth week is set forth as follows and, for the reasons hereinabove stated, considered invalid.

TABLE VIII-X

| | Treatment of the Animals (Data Disregarded) | | | |
|---|---|---|---|---|
| Week No. 5 | Group I (CONTROL) | Group II[a] | Group III[b] | Group IV[c] |
| Week No 5 | | | | |
| No. of animals tested | 23 | 25 | 16 | 17 |
| No. of Measurements | 138 | 150 | 96 | 102 |
| Mean Value Blood Pressure | 134.54 | 137.52 | 143.06 | 142.53 |
| Standard Deviation | 18.09 | 18.14 | 16.05 | 15.42 |
| Standard Error | 3.77 | 3.70 | 4.01 | 3.74 |

Figure 2:
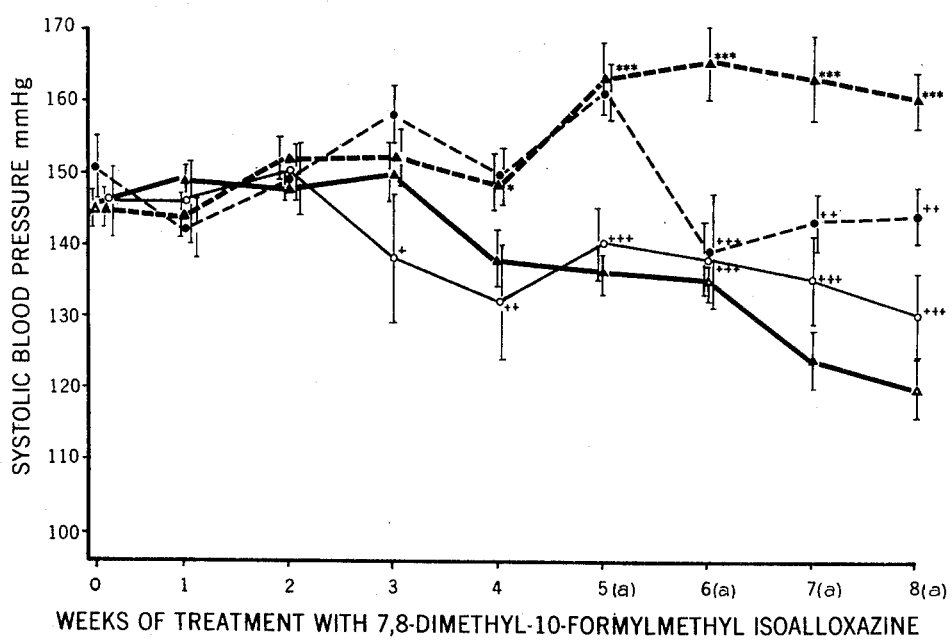
FIG. 2 is a graphic illustration of the effect of 7,8-dimethyl-10-formylmethyl isoalloxazine as an antihypertensive agent for mineralocorticoid-induced hypertensive rats during an 8 week study.

[a] Treated with deoxycorticosterone acetate
[b] deoxycorticosterone acetate + 1.2 mg. 7,8-dimethyl-10-formylmethyl isoalloxazine
[c] deoxycorticosterone acetate + 1.6 mg. 7,8-dimethyl-10-formylmethyl isoalloxazine The weekly mean systolic blood pressure measurements tabulated in Table VIII provide the data points of the graph of FIG. 2. The weekly mean systolic blood pressure measurements of the 2nd week of the conditioning period (Table VII) represents the 0 week on the graph of FIG. 2. The points in FIG. 2 representing the mean blood pressure values of the four groups of animals are designated as follows:

△ - Group I (Control)
▲ - Group II
● - Group III
○ - Group IV

In order to eliminate, as much as possible, variations in the readings of the systolic blood pressure of the animals during the experiments, the animals were warmed with an infra-red lamp (ambient temperature of 35° C. to 40° C.) until the arterial pulse displacements were nearly full scale. The indirect systolic pressure measurements were then obtained by increasing the pressure of the occlusion cuff until the arterial pulse displacements were no longer apparent and then gradually releasing cuff pressure. The cuff pressure at which the first real pulse displacement appeared was defined as the systolic pressure. The systolic pressures were recorded by the same person and at approximately the same time of the day through the entire investigation.

The data of Table VIII, as depicted in FIG. 1, clearly illustrates that the systolic blood pressures of the rats rose significantly after four weeks of biweekly treatment with 3.0 milligrams of deoxycorticosterone acetate. The blood pressure of the rats remained in the hypertensive range until the end of the eighth week of testing (e.g. after nine weeks for the reason stated hereinabove) at which time the animals were sacrificed. The systolic blood pressures of the rats administered deoxycorticosterone acetate averaged about 165±5 mm mercury (standard error of the mean) compared to the controls of about 130±3 mm mercury. The elevation in the systolic blood pressures of the rats noted after the fourth week, when deoxycorticosterone acetate was administered, was not evident when 1.6 milligrams of 7,8-dimethyl-10-formylmethyl isoalloxazine were administered in combination with the deoxycorticosterone acetate to the rats. The systolic blood pressures of the animals treated with the combination of the deoxycorticosterone acetate and the 7,8-dimethyl-10-formylmethyl isoalloxazine averaged about 136±5 mm mercury. Further, the data indicates that not until after the fifth week of treatment was the 1.2 milligram level of the 7,8-dimethyl-10-formylmethyl isoalloxazine effective in reducing the systolic blood pressures of the rats, and after the fifth week the systolic blood pressures were reduced to 142±4 mm mercury. It should be noted that there was no difference in the systolic blood pressures of the four groups of rats prior to the initiation of the drug therapy (0 week on FIG. 2), and that the systolic blood pressures for most of the groups were within approximately 145±4 mm mercury.

In addition to the measurement of the systolic blood pressure of the animals, weekly sodium intake studies were simultaneously carried out on the conditioned rats. The intake of the drinking water, an aqueous 1% sodium chloride solution, was measured during four separate 24 hour periods each week. A mean weekly sodium intake was thus calculated on the basis of the 24 hour drinking water consumption of the animals. The mean weekly sodium intake determinations are tabulated in Table IX and provide the data points of the graph of FIG. 4. The sodium intake from the Purina Rat Chow itself only represented 10% of the sodium intake from the drinking water plus the Rat Chow and thus was not measured in these experiments.

TABLE IX

| | Treatment of the Animals | | | |
|---|---|---|---|---|
| | Group I (CONTROL) | Group II[a] | Group III[b] | Group IV[c] |
| Week No. 1 | | | | |
| No. of separate measurements of drinking water consumptions Mean Value | 30 | 48 | 16 | 16 |
| Sodium Intake mEq/24 hours/Rat | 14.72 | 14.10 | 20.83 | 16.06 |
| Standard Deviation | 4.99 | 5.26 | 4.72 | 2.81 |
| Standard Error | 0.91 | 0.76 | 0.12 | 0.71 |
| Week No. 2 | | | | |
| No. of separate measurements of drinking water consumptions Mean Value | 30 | 44 | 16 | 16 |
| Sodium Intake mEq/24 hours/Rat | 17.18 | 17.42 | 22.62 | 16.90 |
| Standard Deviation | 2.51 | 3.07 | 9.09 | 3.65 |
| Standard Error | 0.46 | 0.46 | 0.94 | 0.23 |
| Week No. 3 | | | | |
| No. of separate Measurements of drinking water consumptions Mean Value | 30 | 46 | 16 | 16 |
| Sodium Intake mEq/24 hours/Rat | 15.46 | 15.20 | 18.55 | 15.31 |
| Standard Deviation | 4.90 | 4.67 | 4.37 | 4.21 |
| Standard Error | 0.90 | 0.69 | 1.09 | 1.05 |
| Week No. 4 | | | | |
| No. of separate Measurements of drinking water consumptions Mean Value | 30 | 46 | 16 | 16 |
| Sodium Intake mEq/24 hours/Rat | 18.95 | 19.03 | 25.84 | 19.38 |
| Standard Deviation | 3.54 | 4.75 | 4.15 | 0.92 |
| Standard Error | 0.65 | 0.70 | 1.04 | 0.23 |
| Week No. 5(A) | | | | |
| No. of separate Measurements of drinking water consumptions Mean Value | 30 | 45 | 16 | 14 |
| Sodium Intake mEq/24 hours/Rat | 16.63 | 20.57 | 20.58 | 18.99 |
| Standard Deviation | 6.13 | 9.23 | 3.64 | 3.89 |
| Standard Error | 1.12 | 1.37 | 0.91 | 1.04 |
| Week No. 6(A) | | | | |
| No. of separate measuremernts of drinking water consumptions Mean Value | 39 | 46 | 16 | 14 |
| Sodium Intake mEq/24 hours/Rat | 15.18 | 18.38 | 18.23 | 18.74 |
| Standard Deviation | 4.16 | 4.71 | 6.22 | 4.46 |
| Standard Error | 0.76 | 0.69 | 1.56 | 1.19 |
| Week No. 7(A) | | | | |
| No. of separate Measurements of drinking water consumptions Mean Value | 30 | 46 | 16 | 14 |
| Sodium Intake mEq/24 hours/Rat | 12.09 | 16.52 | 13.98 | 15.05 |
| Standard Deviation | 1.40 | 4.70 | 3.81 | 2.36 |
| Standard Error | 0.36 | 0.98 | 1.35 | 0.96 |
| Week No. 8(A) | | | | |
| No. of separate measurements of drinking water consumptions Mean Value | 28 | 46 | 16 | 12 |
| Sodium Intake mEq/24 hours/Rat | 10.63 | 20.18 | 23.07 | 22.17 |
| Standard Deviation | 2.64 | 6.72 | 8.27 | 3.56 |

TABLE IX-continued

| | Treatment of the Animals | | | |
|---|---|---|---|---|
| | Group I (CONTROL) | Group II[a] | Group III[b] | Group IV[c] |
| Standard Error | 0.50 | 0.99 | 2.07 | 1.03 |

Figure 4:
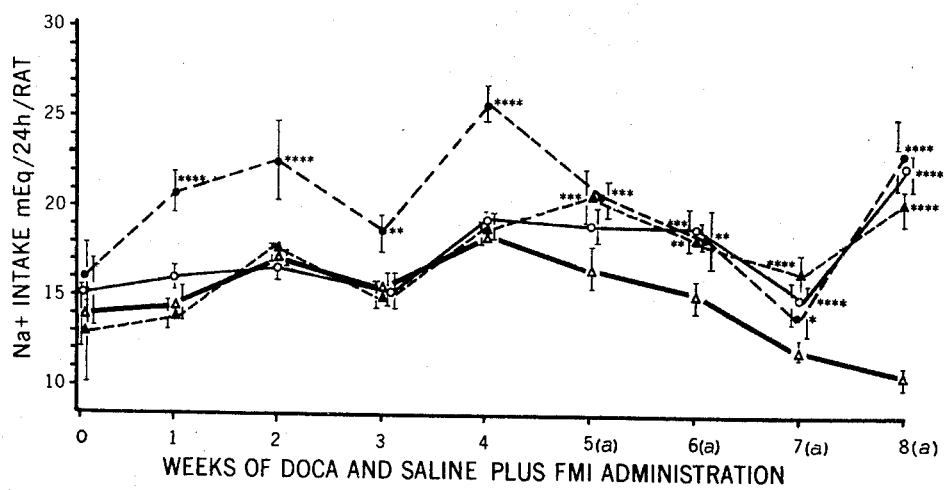
FIG. 4 is a graphic illustration depicting the sodium intake in milliequivalents per 24 hour period per rat of the various groups of rats, including control and treated rats, during an 8 week study.

(A)Data collected after week of disturbance as set forth above.
[a]Treated with deoxycorticosterone acetate
[b]deoxycorticosterone acetate + 1.2 mg. 7,8-dimethyl-10-formylmethyl isoalloxazine
[c]deoxycorticosterone acetate + 1.6 mg. 7,8-dimethyl-10-formylmethyl isoalloxazine The points in FIG. 4 representing the mean weekly sodium intake values of the four groups of animals are designated as follows:

Δ - Group I (Control)
▲ - Group II
● - Group III
○ - Group IV

Blood samples of about 5 milliliters were taken at the end of the 8 week period of investigation via decapitation of the animals and collection of the blood in tubes through a funnel wetted with 25 mM EGTA, ethyleneglycol-bis(-aminoethylether)-N-N'-tetraacetic acid, a free acid manufactured and marketed by the Sigma Chemical Co., St. Louis, Missouri. The EGTA was used to prevent immediate clotting in the funnel stem. Following collection, the blood was allowed to clot and the sera was collected.

Following decapitation, a specimen of approximately 1.5 grams of the left iliopsoas muscle of each rat was excised, weighed and frozen for subsequent tissue electrolyte determination. All sera sodium and potassium determinations were made using an Instrumentation Laboratory Model IL 443 flame photometer (Instrumentation Laboratory, Inc., Lexington, Mass.). For measurement of the sodium and potassium concentrations in the muscel tissue, the specimens of control and treated animals were thawed and processed simultaneously. The wet weight of each sample was taken and the sample dried at 110° C. for 48 hours in glass crucibles. No additional weight loss was found by drying longer than the 48 hour period. After recording the dry weight, the samples were ashed at 550° C. for 24 hours using a Thermodyne-type 1400 furnace and then the samples were cooled.

Following the ashing procedure, the white ashes were digested in 0.5 milliliters of concentrated nitric acid and the contents of the crubibles were evaporated on a hot plate. The contents of the crucibles were again ashed at 550° C. for 24 hours and then cooled; 0.1 milliliter of concentrated nitric acid was added to each crucible; and thereafter, 1.0 milliliter of 0.5 N nitric acid was added. The contents of each crucible were transferred to separate 10.0 milliliter volumetric flasks; each crucible was rinsed twice more with 1.0 milliliter of the 0.5 N nitric acid, thus providing a total liquid volume of 3.1 milliliter; and then each crucible was rinsed three times with deionized water, thereby bringing the total volume of the contents in each volumetric flask to 10.0 milliliters. Te sodium and potassium contents of each flask were determined by a flame photometer, and the sodium and potassium concentrations in the iliopsoas tissue were then expressed in microequivalents per gram dry weight. The water contents of the specimen were calculated by the formula (weight loss after drying per wet weight)×100.

Table X provides a tabulation of the sodium concentration and the potassium concentration detected in the iliopsoas muscles of the sacrificed animals of Groups I through IV.

TABLE X

EFFECT OF NINE WEEKS OF ADMINISTRATION OF 7,8-DIMETHYL-10-FORMYLMETHYL ISOALLOXAZINE ON THE SODIUM AND POTASSIUM CONTENTS OF THE ILIOPSOAS MUSCLE OF DEOXYCORTICOSTERONE ACETATE-SALT HYPERTENSIVE RATS

| Treatment Group No. | Number of Rats | Sodium μeq/q Dry Wt | Potassium μeq/q Dry Wt |
|---|---|---|---|
| I (CONTROL) | 14 | 117 ± 2 | 465 ± 8 |
| II[a] | 21 | 149 ± 3 | 404 ± 6 |
| III[b] | 8 | 138 ± 5 | 406 ± 13 |
| IV[c] | 8 | 132 ± 3 | 401 ± 11 |

[a]Treated with deoxycorticosterone acetate
[b]deoxycorticosterone acetate + 1.2 mg. 7,8-dimethyl-10-formylmethyl isoalloxazine
[c]deoxycorticosterone acetate + 1.6 mg. 7,8-dimethyl-10-formylmethyl isoalloxazine The above tabulated data illustrates that the administration of 1.2 milligrams or 1.6 milligrams of 7,8-dimethyl-10-formylmethyl isoalloxazine, in combination with deoxycorticosterone acetate, reduced the sodium concentration in the iliopsoas muscle of the animals tested. Further, the data indicates that use of the higher dosage of the 7,8-dimethyl-10-formylmethyl isoalloxazine (i.e. 1.6 milligrams) is more effective than the lower dosage of such riboflavin analogue.

The administration of the deoxycorticosterone acetate to the animals increased the water content of the iliopsoas muscle of the animals by an average value of 0.9 percent; whereas the treatment of the animals with deoxycorticosterone acetate in combination with 1.2 milligrams or 1.6 milligrams of 7,8-dimethyl-10-formylmethyl isoallozixine reduced the water content of the iliopsoas muscle of the animals to approximately the same level as the control animals. Table XI summarizes the effect of deoxycorticosterone acetate and the combination of deoxycorticosterone acetate and 7,8-dimethyl-10-formylmethyl isoalloxazine on the water content of the iliopsoas muscle of the test animals.

TABLE XI

INFLUENCE OF NINE WEEKS OF ADMINISTRATION OF 7,8-DIMETHYL-10-FORMYLMETHYL ISOALLOXAZINE ADMINISTRATION ON THE WATER CONTENT OF THE ILIOPSOAS MUSCLE OF DEOXYCORTICOSTERONE ACETATE-SALT HYPERTENSIVE RATS

| Treatment Group No. | Number of Rats | Water Content % |
|---|---|---|
| I (CONTROL) | 14 | 77.07 ± 0.23 |
| II[a] | 21 | 77.76 ± 0.20 |
| III[b] | 8 | 76.75 ± 0.29 |
| IV[c] | 8 | 76.38 ± 0.60 |

[a]Treated with deoxycorticosterone acetate
[b]deoxycorticosterone acetate + 1.2 mg. 7,8-dimethyl-10-formylmethyl isoalloxazine
[c]deoxycorticosterone acetate + 1.6 mg. 7,8-dimethyl-10-formylmethyl isoalloxazine The data set forth in Tables X and XI illustrates that deoxycorticosterone acetate resulted in an average 27 percent increase in the sodium content of the iliopsoas muscle of the animal and an average 0.9 percent increase in the water content of the muscle. Such data suggests that deoxycorticosterone acetate causes a positive sodium balance in the animal. However, the data further suggests that 7,8-dimethyl-10-formylmethyl isoalloxazine effectively reduces the positive sodium balance caused by the deoxycorticosterone acetate.

In addition, Table XII summarizes the effect of deoxycorticosterone acetate and varying amounts of the riboflavin analogue 7,8-dimethyl-10-formylmethyl isoalloxazine on the heart and kidney weights of the treated animals.

TABLE XII

SUMMATION OF THE EFFECT OF NINE WEEKS OF RIBOFLAVIN ANALOGUE 7,8-DIMETHYL-10-FORMYLMETHYL ISOALLOXAZINE ADMINISTRATION ON THE ORGAN WEIGHTS OF DEOXYCORTICOSTERONE ACETATE-SALT HYPERTENSIVE RATS

| Treatment Group No. | Number of Rats | Average Heart wt (g) | Average Heart wt 100g Body wt (g) | Average Kidney wt (g) | Average Kidney wt 100g Body wt (g) |
|---|---|---|---|---|---|
| I (CONTROL) | 14 | 1.52 ± 0.04 | 0.33 ± 0.01 | 2.62 ± 0.10 | 0.57 ± 0.02 |
| II[a] | 21 | 1.63 ± 0.05 | 0.37 ± 0.01 | 2.95 ± 0.12 | 0.65 ± 0.02 |
| III[b] | 8 | 1.73 ± 0.08 | 0.36 ± 0.02 | 3.03 ± 0.11 | 0.64 ± 0.02 |
| IV[c] | 8 | 1.76 ± 0.03 | 0.36 ± 0.01 | 3.47 ± 0.20 | 0.71 ± 0.03 |

[a]Treated with deoxycorticosterone acetate
[b]deoxycorticosterone acetate + 1.2 mg. 7,8-dimethyl-10-formylmethyl isoalloxazine
[c]deoxycorticosterone acetate + 1.6 mg. 7,8-dimethyl-10-formylmethyl isoalloxazine The above data clearly shows that deoxycorticosterone acetate either singularly or in combination with the riboflavin analogue had an effect upon the heart and kidney weights of the animals treated with same.

The data of Examples 1 and 2 illustrates the effectiveness of the riboflavin analogues, namely 7,8-dimethyl-10-(2'-hydroxyethyl) isoallaxazine and 7,8-dimethyl-10-formylmethyl isoalloxazine as antihypertensive agents. In contrast to some traditional antihypertensive agents, the riboflavin analogues do not produce an increase in potassium excretion in treated subjects or a decrease in blood potassium levels. This represents a significant advantage since low levels of blood potassium are sometimes associated with serious disturbances of heart rhythms.

In some rare forms of hypertension, an increased potassium excretion is part of the hypertension syndrome. In treating this type of hypertension, potassium supplements would be added to the riboflavin analogues. Careful monitoring of diet should be included as part of the therapeutic plan when high dosages of riboflavin analogues are administered.

It is clear that the present invention is well adapted to carry out the objects and attain the ends and advantages mentioned, as well as those inherent therein. While a presently preferred embodiment has been described for purposes of this disclosure, numerous changes may be made which will readily suggest themselves to those skilled in the art and which are encompassed within the spirit of the invention disclosed and as defined in the appended claims.

What is claimed is:

1. A method for reducing the blood pressure of a subject suffering from hypertension which comprises administering to the subject an effective, non-toxic dosage of an antihypertensive agent selected from the group consisting of endocyclically substituted and exocyclically substituted isoalloxazines which are competitive inhibitors of the enzyme flavokinase (EC 2.7.1.26).

2. The method of claim 1 wherein the antihypertensive agent is a phosphorylated endocyclically substituted isoalloxazine.

3. The method of claim 1 wherein the antihypertensive agent is a non-phosphorylated endocyclically substituted isoalloxazine.

4. The method of claim 1 wherein the antihypertensive agent is a phosphorylated exocyclically substituted isoalloxazine.

5. The method of claim 1 wherein the antihypertensive agent is a non-phosphorylated exocyclically substituted isoalloxazine.

6. The method of claim 1 wherein the non-toxic dosage of the antihypertensive agent effective to reduce blood pressure is an amount up to about 14 milligrams.

7. The method of claim 6 wherein the dosage of the antihypertensive agent is from about 100 micrograms to about 14 milligrams.

8. The method of claim 1 wherein said antihypertensive agent is an exocyclically substituted isoalloxazine derivative selected from the group consisting of 7,8-dimethyl-10-formylmethyl isoalloxazine and 7,8-dimethyl-10-(2'-hydroxyethyl) isoalloxazine.

9. A method of reducing the blood pressure of a subject suffering from vasoconstrictor hypertension while preventing abnormal excretion of potassium from the body of the subject which comprises administering to the subject an effective, non-toxic dosage of an antihypertensive agent selected from the group consisting of endocyclically substituted and exocyclically substituted isoalloxazines which are competitive inhibitors of the enzyme flavokinase EC 2.7.1.26).

10. The method of claim 9 wherein the antihypertensive agent is a phosphorylated endocyclically substituted isoalloxazine.

11. The method of claim 9 wherein the antihypertensive agent is a non-phosphorylated endocyclically substituted isoalloxazine.

12. The method of claim 9 wherein the antihypertensive agent is a phosphorylated exocyclically substituted isoalloxazine.

13. The method of claim 9 wherein the antihypertensive agent is a non-phosphorylated exocyclically substituted isoalloxazine.

14. The method of claim 9 wherein the non-toxic dosage of the antihypertensive agent effective to reduce blood pressure is an amount of from about 100 micrograms to about 2 milligrams.

15. The method of claim 9 wherein said antihypertensive agent is an exocyclically substituted isoalloxazine derivative selected from the group consisting of 7,8-dimethyl-10-formylmethyl isoalloxazine and 7,8-dimethyl-10-(2'-hydroxyethyl) isoalloxazine.

* * * * *

UNITED STATES PATENT AND TRADEMARK OFFICE
CERTIFICATE OF CORRECTION

PATENT NO. : 4,264,601
DATED : April 28, 1981
INVENTOR(S) : Daniel Trachewsky

It is certified that error appears in the above-identified patent and that said Letters Patent is hereby corrected as shown below:

Column 8, line 67, the word "above" should be --about--.
Column 13, line 26, "mg" should be --g--.

Signed and Sealed this

Thirteenth Day of November 1984

[SEAL]

Attest:

GERALD J. MOSSINGHOFF

Attesting Officer   Commissioner of Patents and Trademarks